United States Patent [19]

Auclair et al.

[11] Patent Number: 4,964,869
[45] Date of Patent: Oct. 23, 1990

[54] ASSEMBLY OF A CERAMIC HEAD ON A METAL ROD FOR A HIP PROSTHESIS

[75] Inventors: Michel Auclair, Bois d Arcy; Christian Prats, Evreux, both of France

[73] Assignee: Ceramiques Techniques Desmarquest, Courbevoie, France

[21] Appl. No.: 372,753

[22] Filed: Jun. 28, 1989

[30] Foreign Application Priority Data

Jun. 28, 1988 [FR] France ................ 88 09042

[51] Int. Cl.$^5$ .................. A61F 2/36; A61F 2/32
[52] U.S. Cl. ........................ 623/23; 623/22
[58] Field of Search ............ 623/16, 18, 22, 23

[56] References Cited

U.S. PATENT DOCUMENTS

| | | | |
|---|---|---|---|
| 4,012,795 | 3/1977 | Doore et al. | 623/23 X |
| 4,058,856 | 11/1977 | Doerre et al. | 623/22 X |
| 4,184,213 | 1/1980 | Heimke | 623/18 |
| 4,318,190 | 3/1982 | Cortesi | 623/23 |
| 4,636,218 | 1/1987 | Fukuura et al. | 623/18 |

Primary Examiner—Ronald Frinks
Attorney, Agent, or Firm—Dennison, Meserole, Pollack & Scheiner

[57] ABSTRACT

An assembly of a ceramic head fixed to a rod, which assembly is a component of a hip prosthesis that has improved distribution of the stresses transferred from the rod to the ceramic head. The ceramic head includes a blind recess, generally in the shape of a truncated cone, into which the male end of the rod is nested, in which this nesting together is provided without play between the ceramic head and the end of the rod in only a portion of the depth of the recess, while in the remaining portion of the recess there is no contact between the ceramic head and the end of the rod.

9 Claims, 1 Drawing Sheet

ASSEMBLY OF A CERAMIC HEAD ON A METAL ROD FOR A HIP PROSTHESIS

FIELD OF THE INVENTION

The invention relates to an assembly of a ceramic head (in general a ball) with a metal rod for a hip prosthesis. This assembly, together with a second part, called an acetabular recess, constitutes an internal prosthesis of the femoral joint.

BACKGROUND OF THE INVENTION

The use of an assembly comprising a ceramic head and a metal femoral rod as a femoral prosthesis is known, one end of the rod being implanted in the femur and the other being nested in a blind recess cut into in the ceramic head. This assembly in general is associated with a natural or artificial acetabular cup supporting the rotation of the ceramic head in order to form an internal prosthesis for the femoral joint.

The blind recess made in the ceramic head (the female part) is customarily of truncated cone shape with a circular cross section and slight conicity; the male part of the femoral metal rod which is to be nested in it has practically the same angle at the apex, so that assembly by nesting the parts together is done without play between the two pieces, the relative rotation of the head on the rod being prevented by various means such as jointing by force, use of adhesives, wedging, brazing, etc.

Because the angle at the apex of the cone is slight, it quite often occurs that during the placement of the two pieces by the physician their alignment is not totally correct; thus instead of having a contact surface between the faces of the female and male pieces, the male piece is actually only in contact with some points on the surface of the recess of the female piece. For the same reasons it also happens that the male piece is not nested in place over all of the bearing surface provided in the recess of the female piece; for example, the apex of the male piece might be incorrectly supported by a point on the surface of the recess which is not located in the bottom of the recess and, at the same time, the contact surface of the male piece might be incorrectly supported on a point of the recess close to the periphery of the ceramic head.

Sometimes the male metal cone and the ceramic recess also have faults in their geometry which cause the contact between the two pieces to occur only at some points so that their placement is not correct.

All of these problems, associated with the placing of the male and female pieces by means of nesting them together, by definition mean that the mechanical stresses due to exterior stress and sustained by the ceramic head are transmitted from the male piece to the femur by means of only a few contact points between the male piece and the recess of the female piece, instead of by means of a contact surface. Thus the stresses supported by the ceramic head are considerably increased at these points and are the cause of a very serious increase of a risk of breaking of the ceramic head. These breaks usually occur in the anterior area, rather than the deep area, of the recess of the ceramic head.

SUMMARY OF THE INVENTION

It is an object of the invention to provide a nesting assembly between the male cone of the metal femoral rod and the conical recess of the ceramic head in such a way as to prevent the risk of breakage of the ceramic head from bad seating and/or faults in the geometry of these two pieces which are in contact.

It is another object to assure a secure seating of the two pieces in the course of their assembly by the physician.

It is still another object to provide a prosthetic femoral assembly comprising a ceramic head and a metal rod having an improved mechanical resistance to breaking based on an optimal distribution of the stresses in the ceramic head.

The invention consists of an assembly of a ceramic head, comprising a blind recess and a male peg nested therein machined on one end of a metal rod, the unit thus obtained joined to an acetabular cup forming an internal prosthesis for the hip joint; allowing optimal distribution of mechanical stresses in the ceramic head, the assembly is characterized in that the nesting of the male peg takes place without play in a first truncated cone-shaped zone of the recess, called the deep contact zone, located towards the center of the ceramic head and having a small apex angle, and in that in a second zone of the recess, called the non-contact zone, extending the first one in the direction of the periphery of the ceramic head and opening towards the exterior, the male peg and the surface of the second zone of the recess are not in contact.

In accordance with the invention the peg or machined end of the metal rod and the recess of the ceramic head in which it is nested are in contact only by means of at most a part of their total lateral surfaces, and the contact is limited to the bottom of the recess. The parts thus in contact are:

- as far as the recess of the ceramic head is concerned, the part of its lateral surface located in the deepest zone of the recess, with the exception of the bottom itself. This part is in the shape of a truncated cone with a small apex angle,
- as far as the peg nested in the recess is concerned, that part of its lateral surface located closest to its free end.

Thus it is apparent that the truncated cone of the deep zone of the recess and the truncated cone of the free end of the peg, cooperating with each other in the assembly, are machined with an identical angle with close tolerances, while in the non-contact zone the surfaces of the recess and the peg which are opposite each other but are not in contact are totally different.

The dimensions of the surfaces in contact are such that there is no play between them and that the male peg will not abut on the bottom of the recess. Thus, the bottom of the blind cavity and the transverse apex surface of the truncated cone of the male peg are not in contact with each other.

Usually, the deep zone of the recess as well as the surface of the male peg in contact with it have a symmetry of revolution around an axis merging with a radius of the ceramic head. The surfaces in contact are preferably of truncated cone shape, but of necessity with apex angles practically identical.

The total apex angle of the common truncated cone is small and generally is between 3 and 10° and preferably is near 6°.

The depth of the bearing surface on which there is contact between the lateral surface of the recess and the corresponding surface of the peg in general comprises between 15% and 80%, preferably between 25 and 70%, of the total depth of the recess. Generally this depth is calculated starting at a point located on the axis of revolution, at a distance such that a free protective space between the bottom of the recess and the apex of the peg is kept to prevent them from coming into contact. It is important that this space have a depth of no more than 2 mm. This protective space is very important because, if the stresses borne by the ceramic head are displaced towards zones with enlarged cross section, this presents a risk of breakage and lessens the effectiveness of the device according to the invention.

The deep contact zone of the recess is elongated in the direction of the periphery of the head by a second zone where all contact with the metal rod is carefully avoided. This contact-free zone is obtained:

- either preferably by machining the recess of the ceramic head in its non-contact zone by increasing the mean diameter, for example machining it with a truncated cone having an apex angle greater than the truncated cone of the contact zone, while the surface of the opposite peg may also be in the shape of a truncated cone with a very small apex angle (in this case the peg may be advantageously machined with a unique truncated cone of a profile constant over the whole of the depth of the two zones) or cylindrical;
- or by machining the peg in the non-contact zone, by reducing the mean diameter, for example with a truncated cone having an apex angle smaller than the truncated cone of the contact zone or with a cylinder, while the recess must always maintain a constant truncated profile over its entire depth.

Thus it becomes clear that in accordance with the invention at least either the recess or the peg have a profile which is not constant over their entire depth; this means that along the depth profile of at least one of the two pieces a break in the line of the slope of the outer surface opposite the surface of the other piece is noted.

In the contact zone the laterally opposite surfaces of the recess and the peg are in contact across their entire surface.

Contact is made by means of a common, non-deformable truncated cone and is total after the two pieces have been put in place by simple nesting together, since the contact surfaces existed from the time of machining; the depth of the contact zone is also constant once this placement has been effected.

The thickness of the existing free disengagement space in the non-contact zone between the surface of the recess and that of the peg in general does not exceed 2 mm and usually 1 mm and sometimes even less; it is constant or variable over the depth of the non-contact zone, after which the profiles of the second zone of the recess and of the zone of the peg facing it are similar, for example, both cylindrical, but not with the same diameter, or different, for example one is cylindrical, the other has a truncated cone shape.

This non-contact zone has a depth, measured on the axis of revolution of the recess, which is deducted from the depth of the contact previously mentioned; thus it is at a minimum equal to 20% of the total depth of the reduced recess of the free protective space. It is accordingly completely different from a non-contact zone, such as found in the prior art, resulting in a slight bevel cut in the edge of the opening of the recess; as a matter of fact, the depth of this bevel generally does not exceed 1 mm and generally is 0.5 mm.

Once the assembly has been put together by jointing, the rotation of the ceramic head on the end of the metal rod is prevented by any known means, such as gluing, forced jointing, wedging, soldering, etc.

FIGS. 1-3 allow a better understanding of the invention.

DETAILED DESCRIPTION OF THE PREFERRED EMBODIMENTS

Figure 1:
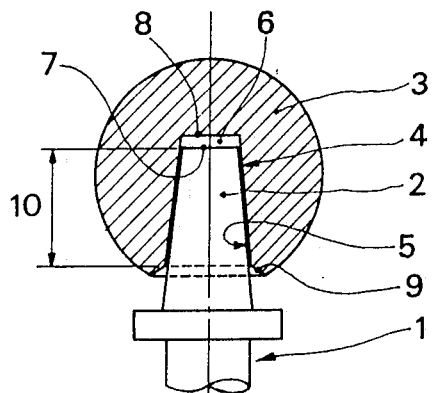
FIG. 1 is an assembly of a ceramic head and metal rod in accordance with the prior art.

In FIG. 1 the metal rod 1 is shown with its machined conical peg 2 designed to be nested completely in the corresponding recess of the ceramic head 3. It can be seen that the surface 4 of the recess and the surface 5 of the end of the metal rod are in contact at a depth 10, which is the total of the depth of the recess, reduced by the small protective space 6 separating the crown 7 of the metal rod 1 from the bottom 8 of the recess of the ceramic head 3, and reduced by the depth of the bevel 9 cut into the edge of the mouth of the recess of the head 3. Since the machined cone 2 of the metal rod and the recess of the ceramic head 3 are in the shape of truncated cones, they are nested in each other without play, resulting in an assembly for a femoral prosthesis.

Figure 2:
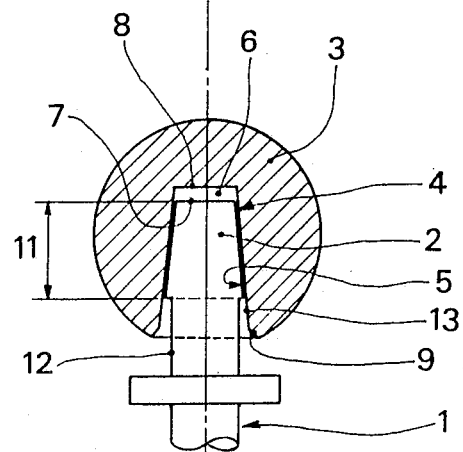
FIGS. 2 and 3 show two ways of realizing the invention.

In FIG. 2, which represents a particular embodiment of the realization of the assembly in accordance with the invention, it can be seen that the recess of the ceramic head is in the shape of a truncated cone over its entire depth. On the other hand, the machined peg 2, which is in contact with the surface 4 of the deep zone of the recess, is in the shape of a truncated cone over a depth 11 which is clearly less than the total depth of the recess; this cone 2 continues by means of a cylindrical section 12 which faces, but does not touch, the second, non-contact zone 13 of the recess. The width of the space existing between the surface of the recess and that of the metal rod is in this case not constant.

Figure 3:
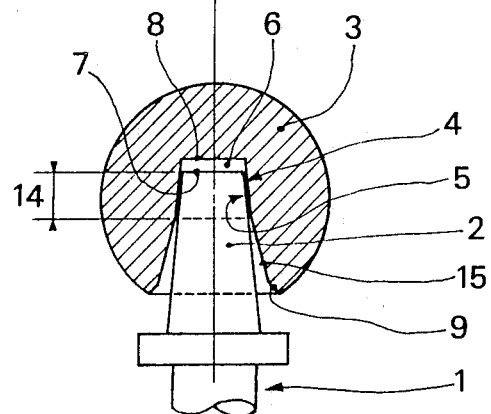

In FIG. 3, which represents another particular embodiment of the realization of the invention, it can be seen that the recess is still in the shape of a truncated cone, that the deep contact zone 14 is much less than in the previous case, and that the second, non-contact zone of the recess was made by cutting a truncated cone-shaped recess 15 into the ceramic head behind the deep zone with a slightly larger apex angle. The cone 2 of the metal rod is in the shape of a truncated cone over the entire depth corresponding to the recess. In this case the width of the space existing between the surface of the recess after the application of the recess and the surface of the metal rod is also not constant.

The assembly in accordance with the invention is applicable to all sintered ceramic heads based on oxides, for example, such as aluminum oxides, zirconium oxides, etc; of carbides, of nitrites such as silicone nitrite, or borates, etc., or their mixtures, even to composite materials (for example carbon —carbon). The head is generally solid, i.e. has no other recesses than the blind recess required for the assembly.

In the same way the metal rod is of a suitable type, for example titanium, stainless steel or other alloys; it can also be made of any material sufficiently strong for such an application, such as composite materials.

The invention is in particular applicable to the making of complete prostheses for hip joints, the acetabular cup into which the ball is placed may be natural or artificial (of metal, ceramics, composite material, synthetic material, etc.); it is also applicable to all connections by means of nesting a metal rod in a blind recess of a ceramic, substantially spheroid head.

EXAMPLES

Comparative static rupture tests were conducted on the heads corresponding to each one of the cases illustrated in FIGS. 1 to 3.

They consisted of the application of a force to a ceramic head 3, assembled with the metal rod 1-2, along the axis of assembly, until the ceramic head was destroyed; they were made in accordance with the procedure described in the French Standardization Plan No. PR.S 90443 dated Feb. 10, 1988, "Pièces fémorales de prothèse de hanche avec tête rapportée: spécifications de la tête et de la partie mâle de emboîtement".

Examples 1,2,3 correspond to practical tests of balls made of sintered aluminum oxide with a diameter of 28 mm and a recess of a depth of 16.5 mm; the deep contact zone has a truncated cone-shaped profile with a bottom 8 of 14 mm diameter and a total apex angle of 6°. The metal femoral rod is made of a titanium-based alloy and has a machined peg, its contact zone has the same apex angle as the recess, but the diameter of its crown 7 is slightly larger than that of the bottom 8 so as to create the small protective space 6 between the crown 7 and the bottom 8, the width of which is 1 mm.

The examples 4 and 5 correspond to tests made on balls of sintered zirconium oxide of 28 mm diameter with a recess having a depth of 20 mm and a protective space 6 of 0.5 mm width under the same conditions as the tests of examples 1 and 2.

EXAMPLE 1 (FIG. 1, previously described)

This illustrates an assembly in accordance with the prior art.

The depth of the contact surface between the cone 2 of the machined metal rod in the form of a truncated cone and the recess corresponding to the ceramic head 3 is 15 mm, taking into account the protective space 6 and the depth of the bevel 9, which 0.5 mm.

Thus, the seat is 100% of the useful depth of the recess.

A plurality of tests were made; the average obtained of the rupture force is 2,960 kg.

EXAMPLE 2 (FIG. 2, previously described)

The seating depth 11 is 10 mm, which is 65% of the total depth of the recess reduced by the width of the protective space 6.

As mentioned above, the non-contact zone was obtained by means of a cylindrical machining 12 by shrinking of the end of the metal rod.

The same tests resulted in an average rupture force of 5,470 kg.

EXAMPLE 3 (FIG. 3, previously described)

The seating contact depth 14 is 5 mm, which is 33% of the total depth of the recess reduced by the depth of the protective space 6.

As mentioned above, the non-contact zone was obtained by means of truncated cone-shaped machining of the second zone of the recess with an angle slightly larger than that of the truncated cone of the contact zone.

The same tests resulted in an average rupture force of 4,600 kg.

EXAMPLE 4 (FIG. 1, previously described)

This illustrates an assembly in accordance with the prior art, this time applied to balls of sintered zirconium oxide. The depth of the contact surface between the cone 2 of the machined metal rod and the recess corresponding to the ceramic head is 19 mm, once the protective space 6 of 1 mm and the depth of the bevel 9, which is 0.5 mm, are deducted.

The seat is 100% of the useful depth of the recess.

The same tests led to an average value of the rupture force of 8,750 kg.

EXAMPLE 5 (FIG. 2, previously described)

The depth 11 of the seat is 12 mm, which is 62% of the total depth of the recess reduced by the protective space 6.

The non-contact zone was obtained by means of a cylindrical machining 12 by shrinking of the peg located on the end of the metal rod.

The same tests resulted in an average rupture force of 12,900 kg.

What is claimed is:

1. An assembly for use in combination with an acetabular cup for forming an internal prosthesis for a hip joint, said assembly comprising:
   a ceramic head having extending from its outer surface a blind-ended recess in the shape, at least at the blind end of said recess, of a truncated cone of predetermined, small apex angle and dimensions; and
   a peg formed at the end of a rod and inserted within said recess to a predetermined depth, said peg having at least a distal end formed in the shape of a truncated cone of apex angle corresponding to the apex angle of said recess, and dimensions such that said peg is nested in said recess in a deep contact zone located toward the center of said ceramic head, said deep contact zone being about 15% to 80% of the depth of insertion of the peg in the recess, a non-contact zone between the peg and the recess being located between said deep contact zone and the surface of said ceramic head;
   said assembly providing optimal distribution of stresses from the peg to the ceramic head.

2. An assembly in accordance with claim 1, wherein the depth of the non-contact zone is obtained by the forming of the complementary part comprising the peg of the rod.

3. An assembly in accordance with claim 1 or 2, wherein the non-contact zone is obtained by the forming of the recess of the ceramic head in the non-contact zone.

4. An assembly in accordance with claim 1 or 2, additionally comprising a free protective space (6) between the blind end of the recess and the end of the peg which is inserted to said predetermined depth.

5. An assembly in accordance with claim 1 or 2, wherein the contact zone comprises between 25 and 70% of the depth of insertion of the peg in the recess.

6. An assembly in accordance with claim 1 or 2, wherein the head (3) is formed from a hard material selected from the group consisting of oxides, carbides, nitrides and composite materials.

7. An assembly in accordance with claim 1 or 2, wherein the apex angle of the truncated cone comprises between 3 and 10°.

8. An assembly in accordance with claim 7 wherein the apex angle is about 6°.

9. An assembly in accordance with claim 6 wherein the oxides comprise aluminum oxide or zirconium oxide, the nitrides comprise silicon nitride and the composite materials comprise carbon-carbon composites.

* * * * *